US008524507B2

(12) United States Patent
Kennedy

(10) Patent No.: US 8,524,507 B2
(45) Date of Patent: Sep. 3, 2013

(54) METHOD FOR DETECTING A TARGET MOLECULE IN A BIOLOGICAL SAMPLE

(75) Inventor: David J. Kennedy, Newbury, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 365 days.

(21) Appl. No.: 12/859,715

(22) Filed: Aug. 19, 2010

(65) Prior Publication Data

US 2011/0045606 A1 Feb. 24, 2011

Related U.S. Application Data

(60) Provisional application No. 61/235,261, filed on Aug. 19, 2009.

(51) Int. Cl.
*G01N 33/543* (2006.01)
(52) U.S. Cl.
USPC ....... 436/518; 435/40.5; 435/40.52; 436/501; 436/530; 436/531; 436/169; 436/809
(58) Field of Classification Search
None
See application file for complete search history.

(56) References Cited

U.S. PATENT DOCUMENTS

| 4,588,682 | A | 5/1986 | Groet et al. |
| 5,866,417 | A | 2/1999 | Matyas et al. |
| 2004/0081987 | A1* | 4/2004 | Knezevic et al. ............... 435/6 |
| 2007/0098601 | A1 | 5/2007 | Mabuchi et al. |
| 2007/0243628 | A1 | 10/2007 | Mabuchi et al. |

FOREIGN PATENT DOCUMENTS

| JP | 09-234100 A | 9/1997 |
| WO | WO-02/48674 A2 | 6/2002 |

OTHER PUBLICATIONS

Endo et al., "Blotting Method Using Nitrocellulose Sheets for Immunohistochemical Detection of Soluble Thyroid Antigens", *The Journal of Histochemistry and Cytochemistry*, 37:547-549, 1989.

* cited by examiner

*Primary Examiner* — Chris L Chin
(74) *Attorney, Agent, or Firm* — Tarolli, Sundheim, Covell & Tummino LLP

(57) ABSTRACT

A method is provided for detecting a target molecule in a biological sample. One step of the method includes immobilizing the biological sample on a membrane. Next, the membrane-bound biological sample is contacted with at least one detection moiety. The membrane-bound biological sample is then separately mated with a substrate and the target molecule detected. At least one step of the method is performed under positive pressure or a vacuum.

14 Claims, 5 Drawing Sheets

A

B

METHOD FOR DETECTING A TARGET MOLECULE IN A BIOLOGICAL SAMPLE

RELATED APPLICATION

This application claims priority from U.S. provisional patent application Ser. No. 61/235,261, filed on Aug. 19, 2009, the subject matter of which is hereby incorporated by reference in its entirety.

TECHNICAL FIELD

The present invention relates generally to immunohistochemical (IHC) and immunohistofluorescent assays, and more particularly to rapid and efficient IHC methods for detecting a target molecule in a biological sample.

BACKGROUND OF THE INVENTION

The use of gel electrophoresis is currently the ubiquitous technique for the separation of biological materials. Typical applications include separation of nucleic acid fragments of various sizes either in the context of sequence determination, detection of polymorphisms, or verification of sizes in other contexts. Other frequently used applications include separation of proteins, verification of homogeneity or purity, identification of post-translational modifications, and confirmation of molecular weight.

In all of these procedures, mixed samples of proteins or nucleic acids are applied to electrophoretic gels and the components separated by application of an electric field across the gel. Regardless of the manner in which the gel is developed, the resulting pattern of migration of the proteins or nucleic acids contained in the sample must be detected in some manner.

To conduct this detection for proteins, the gel support is typically contacted with a blotting membrane to which the entities are transferred as they appear on the gel. The "spots" are then detected, at a minimum, by blocking the membrane with a protein or detergent solution to reduce non-specific binding. The biological entity is then incubated with an antibody specific for the antigen on the membrane. The membrane is then extensively washed to remove any contaminants, unbound blocking proteins, and antibodies. Next, the membrane is treated and incubated with a secondary enzyme-, radioisotope-, fluorophore-, or biotin-conjugated antibody specific for the primary antibody. The membrane is again extensively washed to remove any unbound secondary antibody. A detection reagent, generally a chromogenic, chemiluminescent, fluorescent, radiological, or streptavidin-labeled material, is then applied which either binds to, or is a substrate of the enzyme-conjugate. Lastly, the appropriate detection device is used to determine the presence, absence, position, quantity, etc. of the biological entity.

Furthermore, in order to detect biological entities within the context of an organ, tissue, cell, etc., current immunohistochemical techniques use a process similar to that generally outlined above. Typical applications include identification of biological entities or their location in histological sections or preparations of tissues, organs cells, organisms etc., or verification of biological entities in other contexts.

In these procedures, histological sections or preparations are applied to glass slides. Regardless of the manner in which the histological sections or preparations are applied to glass slide, the resulting pattern, identification, location, etc. of the biological entities contained in the sample must be detected in some manner.

To conduct this detection, the biological entity on the glass slide is incubated with an antibody specific for the antigen on the histological preparation. The glass slide is then extensively washed to remove any contaminants, unbound blocking proteins, and antibodies. Next, the histological preparation/glass slide is treated and incubated with a secondary enzyme-, radioisotope-, fluorophore-, or biotin-conjugated antibody specific for the primary antibody. The membrane is again extensively washed to remove any unbound secondary antibody. A detection reagent, generally a chromogenic, chemiluminescent, fluorescent, radiological, or streptavidin-labeled material, is then applied which either binds to, or is a substrate of the enzyme-conjugate. Lastly, the appropriate detection device is used to determine the presence, absence, position, quantity, etc. of the biological entity.

The last several steps of these processes generally take from 3-6 hours to overnight, depending on the speed of the reaction between the selected reagents, the membrane composition, and the biological entity. The process requires multiple incubation periods of the membrane on a rocking or other suitable mixing platform. It is a lengthy process that most researchers dislike and which consumes a large volume of reagents.

SUMMARY OF THE INVENTION

According to one aspect of the present invention, a method is provided for detecting a target molecule in a biological sample. One step of the method includes immobilizing the biological sample on a membrane. Next, the membrane-bound biological sample is contacted with at least one detection moiety. The membrane-bound biological sample is then separately mated with a substrate, followed by detection of the target molecule. At least one step of the method is performed under vacuum or positive pressure.

According to another aspect of the present invention, an immunohistochemical method is provided for detecting a target protein in a biological sample. One step of the method includes immobilizing the biological sample on a membrane. Next, the membrane-bound biological sample is contacted with at least one detection moiety. The membrane-bound biological sample is then separately mated with a substrate, followed by detection of the target protein. At least one step of the method is performed under vacuum or positive pressure.

According to yet another aspect of the present invention, a method is provided for detecting a plurality of different target proteins in a biological sample. One step of the method includes contacting the biological sample with a plurality of different capture moieties. The plurality of different capture moieties is reactive against the plurality of different target proteins. Next, the biological sample is contacted with a membrane having a second plurality of different capture moieties bound thereto. The second plurality of different capture moieties is reactive against the plurality of different target proteins. The membrane is then contacted with a plurality of different detection moieties. The plurality of different detection moieties is reactive against the plurality of different capture moieties. The plurality of different target proteins is then detected. At least one step of the method is performed under vacuum or positive pressure.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
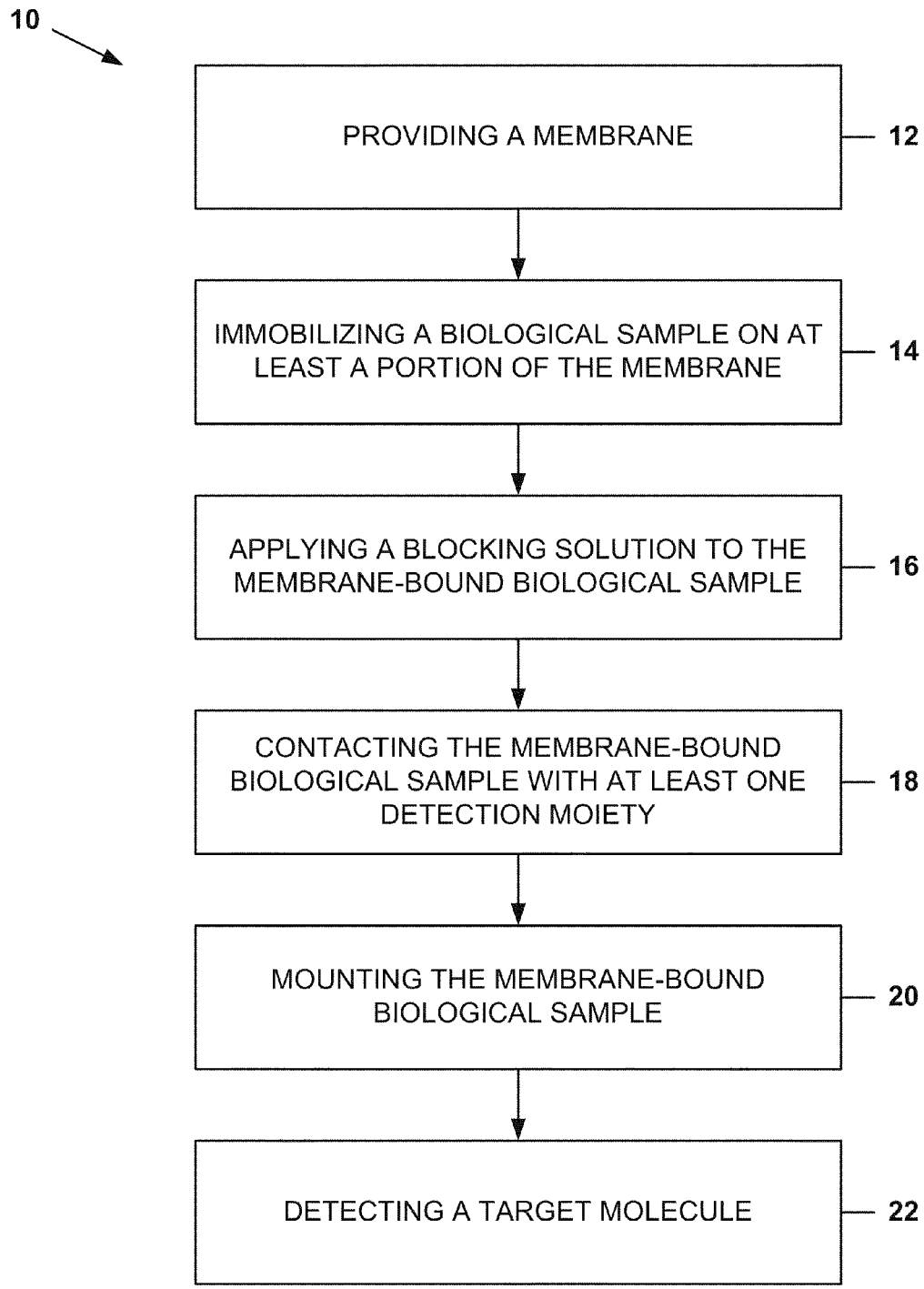
FIG. 1 is a process flow diagram illustrating a method for detecting a target molecule in a biological sample according to one aspect of the present invention.
Figure 2:
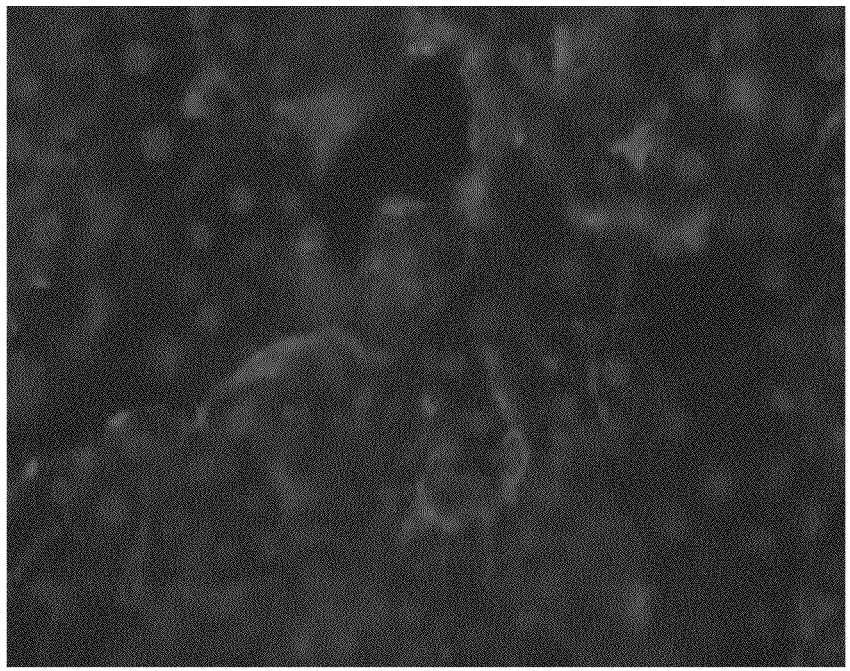
FIG. 2A is a fluorescent micrograph of a murine liver section stained with Actin (red) and DAPI (blue) according to the present invention. This section was prepared using 1% bovine serum albumin (BSA) in tris-buffered saline TWEEN-20 (TBS-T) as the blocking buffer for all reagents.
FIG. 2B is a fluorescent micrograph showing staining for secondary antibody alone as a control for specificity in FIG. 2A. This section was prepared using 1% BSA in TBS-T as the blocking buffer for all reagents.
Figure 2:
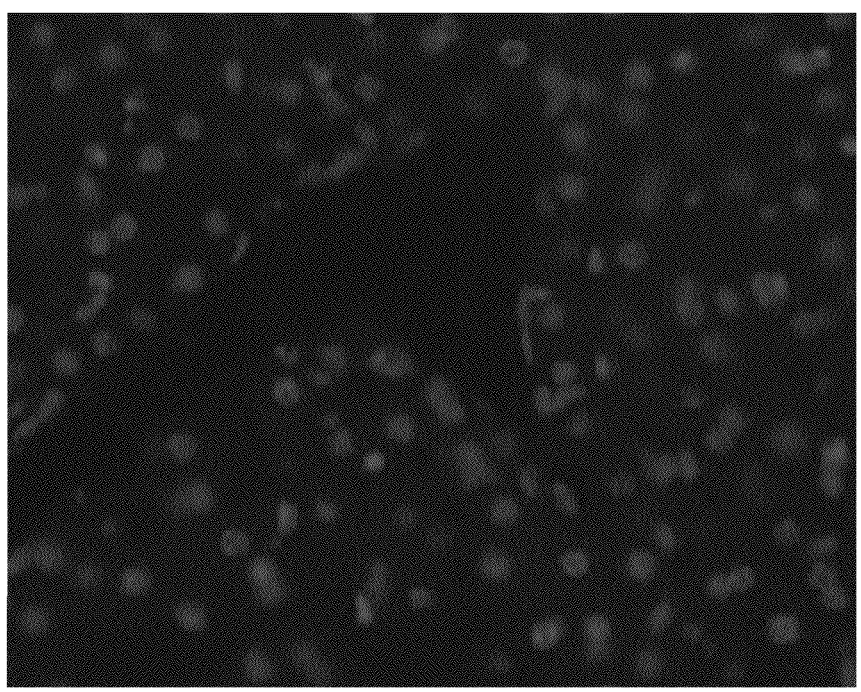
Figure 3:
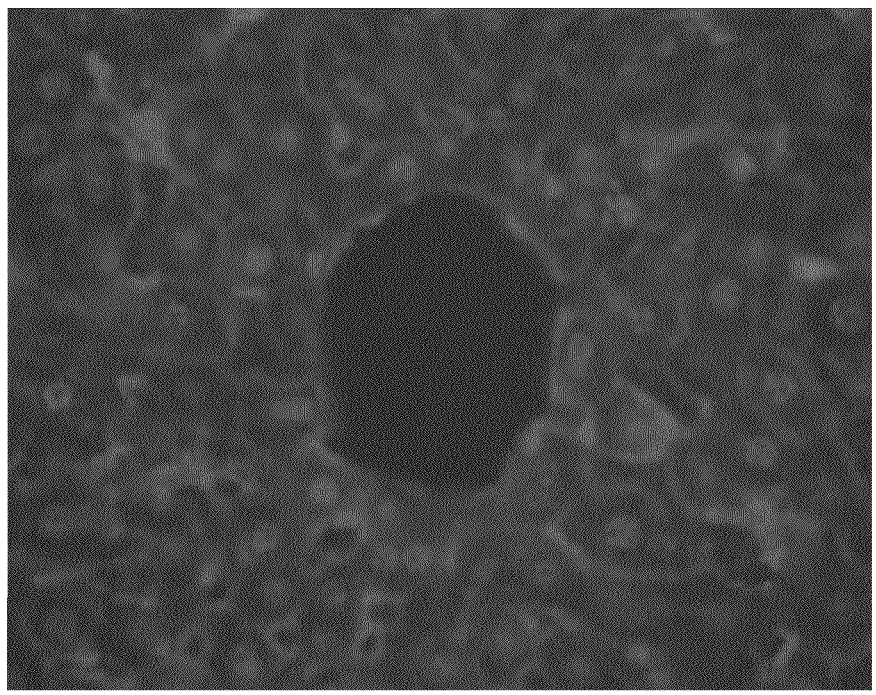
FIG. 3A is a fluorescent micrograph of a murine liver section stained with Actin (red) and DAPI (blue) according to the present invention. This section was prepared using 1% normal goat serum in TBS-T as the blocking buffer for all reagents.
FIG. 3B is a fluorescent micrograph showing staining for secondary antibody alone as a control for specificity in FIG. 3A. This section was prepared using 1% normal goat serum in TBS-T as the blocking buffer for all reagents.
Figure 3:
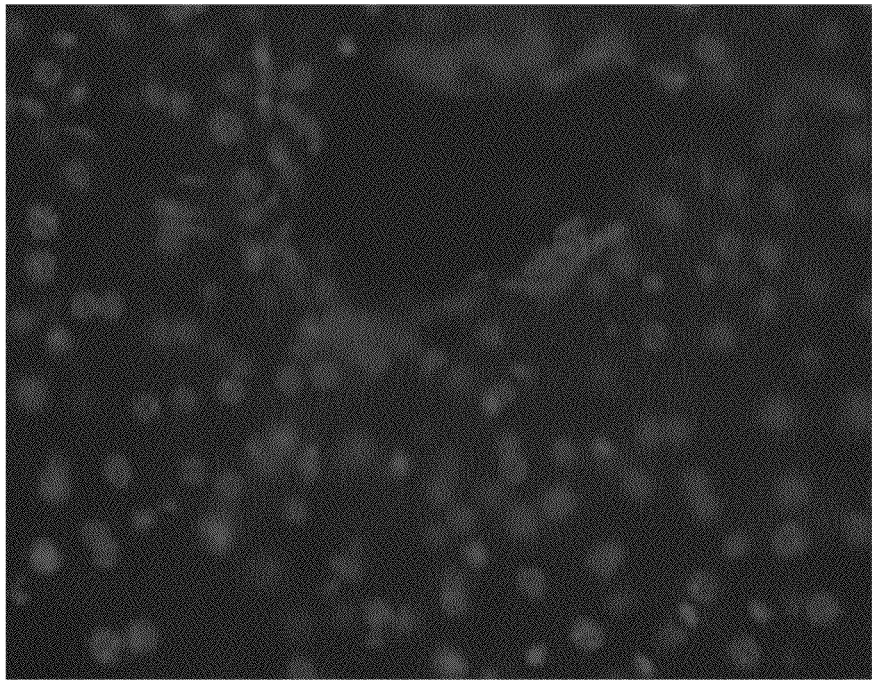

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "target molecule" can refer to any molecule that is capable of binding to or interacting with a capture or detection moiety. Examples of target molecules can include nucleic acids, polypeptides, proteins, carbohydrates, and small molecules.

As used herein, the term "protein" can refer to an oligopeptide, peptide, polypeptide, or to a fragment, portion, or subunit of any of these, and to naturally occurring or synthetic molecules. The term "protein" can also include amino acids joined to each other by peptide bonds or modified peptide bonds, i.e., peptide isosteres, and may contain any type of modified amino acids. Additionally, the term "protein" can include peptides and polypeptide fragments, motifs and the like, glycosylated polypeptides, and all "mimetic" and "peptidomimetic" polypeptide forms.

As used herein, the term "subject" can refer to any organism including, but not limited to, human beings, rats, mice, dogs, goats, sheep, horses, monkeys, apes, pigs, rabbits, cattle, fish, insects, bacteria, viruses, etc.

As used herein, the term "antibody" is used in the broadest sense and can include polyclonal antibodies, monoclonal antibodies, and epitope binding antibody fragments thereof so long as they exhibit the desired binding specificity.

As used herein, the term "biological sample" is used in its broadest sense and can refer to a bodily sample obtained from a subject (e.g., a human). For example, the biological sample can include a "clinical sample", i.e., a sample derived from a subject. Such samples can include, but are not limited to: peripheral bodily fluids, which may or may not contain cells, e.g., blood, urine, plasma, mucous, bile pancreatic juice, supernatant fluid, and serum; tissue or fine needle biopsy samples; and archival samples with known diagnosis, treatment and/or outcome history. Biological samples may also include sections of tissues, such as frozen sections taken for histological purposes. The term "biological sample" can also encompass any material derived by processing the sample. Derived materials can include, but are not limited to, cells (or their progeny) isolated from the biological sample and proteins extracted from the sample. Processing of the biological sample may involve one or more of, filtration, distillation, extraction, concentration, fixation, inactivation of interfering components, addition of reagents, and the like.

The present invention relates generally to immunohistochemical (IHC), immunohistofluorescent, and membrane-based array assays, and more particularly to rapid and efficient IHC methods for detecting at least one target molecule in a biological sample. As representative of one aspect of the present invention, FIG. 1 illustrates a method 10 for detecting a target molecule (e.g., a protein) in a biological sample. As opposed to conventional IHC and immunohistofluorescent assays, which use tissues fixed to a treated glass slide for target molecule detection (e.g., protein detection), the method 10 includes a membrane-bound substrate (e.g., a glass slide) upon which standard detection assays can be performed. Consequently, the method 10 provides a rapid, efficient, and convenient approach for detecting target molecules (e.g., proteins) in time critical applications, such as identifying tumor markers in preserved or fresh frozen surgical specimens or in other biological samples, such as urine, serum, plasma, cell lysates, etc.

Referring to FIG. 1, Step 12 of the method 10 includes providing a membrane having a first major surface oppositely disposed from a second major surface. The membrane can be comprised of any one or combination of porous materials suitable for immobilization of a target molecule, such as nitrocellulose, polyvinylidene fluoride (PVDF), and polyethersulfone (PES). One having ordinary skill in the art will appreciate that the membrane can have other characteristics to facilitate immobilization of a target molecule and reduce reagent consumption. Examples of such membranes are disclosed in U.S. Patent Publication Nos. 2007/0243628 A1 (hereinafter, "the '628 application") and 2007/0098601 A1 (hereinafter, "the '601 application"), the entireties of which are hereby incorporated by reference. For instance, the membrane can comprise a hydrophilic DURAPORE membrane (Millipore Corporation, Billerica, Mass.) formed from PVDF. Alternatively, the membrane can comprise a hydrophilic EXPRESS membrane (Millipore Corporation, Billerica, Mass.) formed from PES.

At Step 14, a biological sample is immobilized on at least a portion of the membrane. In one example of the present invention, the biological sample can be contacted with, and bound to, a portion of the first major surface of the membrane. The biological sample can be obtained during a surgical procedure, such as a biopsy (e.g., a biopsied section of tumor tissue). Alternatively, the biological sample can be embedded with a material, such as OCT resin or paraffin. The biological sample can be placed into contact with a portion of the first major surface immediately after collection or, alternatively, the biological sample can be frozen, stored for a desired period of time, and then contacted with a portion of the first major surface of the membrane. For example, a plurality of OCT-embedded frozen sections of tumor tissue (e.g., of about 8 micrometers in thickness) can be placed onto the first major surface of the membrane.

It will be appreciated that biological samples (e.g., tissue sections) of various dimensions can be affixed to the membrane. For example, some tumors, such as squamous cell carcinoma (SCC) can vary in size from a few millimeters to several centimeters in diameter. Currently, if SCC tumors having any diameter larger than a conventional glass microscope slide (e.g., 25 mm×75 mm) are resected (as in the Mohs surgical technique), the tissue section must be further subdivided into smaller portions to accommodate the dimensions of the glass microscope slide. According to one aspect of the present invention, such tissue sections can be processed in their entirety on the same membrane as malleable materials, such as the membranes disclosed herein can be easily sized (e.g., cut) with more facility than conventional materials (i.e., glass).

After contacting the biological sample with the first major surface of the membrane, the biological sample is physically, electrically, and/or chemically bound to the first major surface. The biological sample can be bound to the first major surface using any one or combination of known techniques, such as drying, electrical transfer preceded by SDS treatment, chemical fixation (e.g., formalin), etc. Where the biological sample is embedded with a material (e.g., OCT resin or paraffin), the embedded material can be removed by washing the membrane-bound biological sample with a buffered solution (i.e., for OCT-embedded samples) or by deparafinization (i.e., for paraffin-embedded samples). In one example of the method 10, frozen tissue samples previously placed on the first major surface of the membrane can be bound by drying at approximately room temperature for about 30 minutes (or less).

In another example of the method 10, a paraffin-embedded tissue section mounted on a membrane can be deparafinized and processed for immunofluorescence or IHC target molecule detection. To do so, one or more tissue sections disposed on a membrane can be deparafinized using a standard deparafinization protocol. Such a protocol can include, for example, taking at least one paraffin-embedded tissue section through rehydration and dehydration washes with about 100% xylene (e.g., about two times for about 10 minutes each), about 100% ethanol (e.g., about two times for about 5 minutes each), about 90% ethanol (e.g., about two times for about 5 minutes each), about 80% ethanol (e.g., about one time for about 5 minutes each), about 70% ethanol (e.g., about one time for about 5 minutes each), PBS (e.g., about three times for about 5 minutes each), an antigen retrieval step (e.g., proteinase K for about 5 minutes or another optimal antigen-specific antigen retrieval method), hydrogen peroxide/methanol treatment (e.g., about 3% final concentration of hydrogen peroxide made-up in a stock solution of methanol), and PBS (e.g., about three times for about 5 minutes each). After this or a similar deparafinization protocol, the tissue section(s) may be ready for further processing and immunofluorescence or IHC detection.

It will become apparent to those skilled in the art that the foregoing deparafinization protocol can be employed for deparafinizing tissue sections mounted on membranes (e.g., for laser capture dissection microscopy). It should also be appreciated that this technique, when combined with the remainder of the method 10, can yield significant time savings as the reagents listed in the steps above have access to both sides of the tissue section via the porous membrane (i.e., as opposed to only the top surface exposure afforded by a glass slide). Further, if any or all of the above-described steps is/are performed under vacuum (i.e., negative pressure) or positive pressure, there will be significant time savings over standard deparafinization techniques for IHC techniques that include paraffin-embedded, fixed tissue(s).

It will be appreciated that the membrane can be modified prior to immobilization of the biological sample thereon to facilitate detection of the target molecule. For example, at least one capture moiety that is reactive against a particular target molecule can be immobilized on the first major surface of the membrane. In one example of the present invention, the capture moiety can comprise an antibody that is reactive against a particular target molecule, such as a protein. Methods for immobilizing antibodies to substrates (e.g., membranes) are well known in the art.

Once the biological sample is bound to the first major surface of the membrane, the membrane-bound biological sample is blocked, washed, and contacted with at least one detection moiety at Steps 16-18. One or more of Steps 16-18 can be performed using known and/or commercially available immunoassay techniques and/or kits. To facilitate rapid and efficient blocking, washing, and detection moiety binding without compromising blot quality, a pressure-assisted regiment (e.g., vacuum or positive gas pressure) can be used, such as those disclosed in the '628 and '601 applications and commercially available as the SNAP i.d. protein detection system (Millipore Corporation, Billerica, Mass.).

At Step 16, the membrane-bound biological sample is contacted with a blocking solution. Before contacting the membrane-bound biological sample with the blocking solution, however, the membrane-bound biological sample can be rehydrated with phosphate buffered solution (PBS) and then transferred to a SNAP i.d. holder. After transferring the membrane-bound biological sample, the blocking solution is contacted with the membrane-bound biological sample for a desired period of time (e.g., about 20 seconds). Examples of blocking agents used to form the blocking solution can include casein, bovine serum albumin (BSA), non-fat dairy milk (generally about 1-5%) in a Tris buffer saline solution with TWEEN surfactant (TBS-T solution) or PBS with TWEEN surfactant (PBS-T solution). In one example of the method 10, the membrane-bound biological sample can be washed once with TBS-T (e.g., about 20 seconds) and then blocked using either about 1% BSA dissolved in TBS-T or about 1% normal goat serum dissolved in TBS-T.

After the blocking solution has been applied to the membrane-bound biological sample for a desired period of time, the membrane-bound biological sample is contacted with at least one detection moiety at Step 18. Depending upon the nature of the target molecule, the desired specificity of the reaction, and the associated reaction conditions, the at least one detection moiety can comprise a primary antibody or a secondary antibody. For instance, a primary antibody can specifically bind to the target molecule, and a secondary antibody can specifically bind to the primary antibody. Also depending upon the nature of the target molecule, the desired specificity of the reaction, and the associated reaction conditions, the primary and/or secondary antibodies can be conjugated or unconjugated with a detectable label. For example, the first and/or second antibodies can be conjugated to horse radish peroxidase (HRP) and then developed with a chemiluminescent reagent (e.g., DAB).

The detectable label can be selected such that it generates a signal, which can be measured and whose intensity is related to the amount of bound antibody. The conjugation of such labels with antibodies is a standard manipulative procedure for one of ordinary skill in immunoassay techniques. See, e.g., O'Sullivan et al. "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166. For example, labeled antibodies can be prepared by incorporation of, or conjugation to, a label that is directly or indirectly detectable by spectroscopic, photochemical, biochemical, immunochemical, electrical, optical (e.g., light microscopy), or chemical means. Examples of detectable labels can include, but are not limited to, various ligands, chromophores, radionuclides, fluorescent dyes, chemiluminescent agents, microparticles, enzymes, calorimetric labels, magnetic labels, and haptens. Detectable labels can also include biological molecules, such as molecular beacons and aptamer beacons.

In one example of the present invention, a detection moiety comprising an unconjugated primary antibody can be contacted with the membrane-bound biological sample at an appropriate dilution (e.g., approximately 1:200 in approximately 1% BSA/TBS-T) and incubated for a desired period of time (e.g., approximately 10 minutes). After incubation with the primary antibody, the membrane-bound biological sample can be washed any number of times (e.g., three times for about 60 seconds) with a buffered solution (e.g., TBS-T). Next, the membrane-bound biological sample can be contacted with a fluorescently-conjugated secondary antibody that specifically binds to the primary antibody. The secondary antibody can be contacted with the membrane-bound biological sample at desired dilution (e.g., about 1:200 in about 1% BSA/TBS-T) and for a desired period of time (e.g., about 10 minutes). The membrane-bound biological sample can then be washed any number of times (e.g., three times for about 60 seconds) with a buffered solution (e.g., TBS-T).

Advantageously, the use of a pressure-assisted regiment (e.g., the SNAP i.d. protein detection system) for one or more of Steps 16-18 significantly decreases the time and volume of reagents needed for blocking, washing, and detection moiety binding. As compared to conventional target molecule detection assays (e.g., Western blots), where diffusion is the primary means of reagent transport, the supply and removal of reagents to and from the membrane under positive pressure or a vacuum (e.g., negative pressure) enables completion of the blocking, washing, and detection moiety binding steps in significantly reduced time without compromising blot quality.

At Step 20, at least a portion of the membrane-bound biological sample is mounted to a substrate, such as a glass microscope slide. One skilled in the art will appreciate that the substrate can alternatively be comprised of one or a combination of materials, such as a solid or porous metal and/or plastic. Examples of such materials can include commercially available laser microdisection slides, which can be comprised of polyethylene naphthalate, polyethylene terephthalate, or polyester. Such laser microdisection membranes can be mounted on glass slides or supported by metal and/or plastic frames (Leica Microsystems Inc., Bannockburn, Ill.). Additionally, one skilled in the art will appreciate that the substrate can alternatively be directly mounted to these materials, such as a membrane supported by a metal and/or plastic frame, as is standard practice for the placement of tissue sections on laser microdisection slides prior to processing.

Prior to mounting the membrane-bound biological sample, the portion of the membrane including the bound biological sample can be resected or sectioned from the remainder of the membrane using, for example, scissors or a scalpel. Additionally or optionally, the membrane-bound biological sample can be treated with an appropriate counter stain and mounting medium at Step 20. In one example of the method 10, the membrane-bound biological sample can be mounted on a glass slide using VECTASHIELD mounting media with DAPI (Vector Laboratories, Burlingame, Calif.) (e.g., about 60 seconds). A glass coverslip can then be placed over the membrane-bound biological sample and the coverslip sealed with acrylic nail polish.

After mounting the membrane-bound biological sample, the target molecule (e.g., protein) is detected at Step 22 using a detection method appropriate to the label. Where the label is a fluorochrome, for example, the glass slide can be taken to a microscope capable of fluorescent detection (e.g., immunohistofluorescence). Examples of fluorescent microscopes are known in the art (e.g., Olympus BX61 and Nikon TE2000 microscopes). Using a fluorescent microscope, for example, the target molecule can be illuminated with light of a specific wavelength (or wavelengths), which is absorbed by the fluorochrome(s) and thereby causes the fluorochrome(s) to emit a longer wavelength (or wavelengths) of light (i.e., of a different color than the absorbed light) and facilitate visualization.

In another example of the present invention, the method 10 can be used to detect a target protein in a biological sample comprised of living cells that are cultured directly on a membrane. Currently, IHC methods can be performed on living cells that have been cultured and fixed on glass slides using commercially available chamber slide systems, such as the Lab-Tek® Chamber Slide™ System (Nalge Nunc International, Rochester, N.Y.). Performing IHC analysis on cells prepared using such commercially available chamber slide systems is cumbersome as it often requires multiple incubation periods (e.g., on a rocking or other suitable mixing platform), is time consuming, and requires a large volume of reagents. As described in more detail below, the pressure-assisted regimen of the present invention permits IHC analysis on living cells for target protein detection that significantly decreases the time and volume of reagents needed without compromising blot quality.

As opposed to conventional chamber slide systems that culture cells on glass slides, the method 10 of the present invention can begin by culturing a biological sample comprised of living cells on a membrane, such as a nitrocellulose or PVDF membrane. Alternatively, the membrane can be part of a Costar® Transwell® Insert, which is commercially available from Corning, Inc. (Lowell, Mass.). The biological sample can be any one or combination of living cells that is/are capable of being grown in culture. For example, the biological sample can be comprised of LLC-PK1 pig kidney proximal tubular cells or primary cells isolated from a primary source (e.g., cardiac fibroblasts isolated from heart tissue or macrophages isolated from the peritoneum).

After culturing the cells to a desired confluency on the membrane, all or only a portion of the membrane can be transferred to a SNAP i.d. holder where, under vacuum or positive pressure, the cells are washed to remove the culture media (e.g., with PBS buffer) and then fixed using a fixative agent (e.g., 4% paraformaldehyde for about 30 minutes at about room temperature, or methanol fixation using pre-cooled methanol for about 10 minutes at about 4° C.). After fixation, the cells can be rinsed again with a buffer (e.g., PBS), followed by the addition of a blocking agent (e.g., about 20 mM sodium phosphate buffer at about pH 7.4 containing about 150 mM sodium chloride, about 0.3% triton-X-100, and about 16% v/v filtered normal goat serum) to reduce non-specific binding of one or more detection or capture moieties.

Next, the cells can be permeabilized with a permeabilizing agent (e.g., PBS containing about 0.1 mM calcium chloride, about 1 mM magnesium chloride, about 0.3% triton-X-100, and about 0.1% bovine serum albumin). The cells can then be contacted with at least one capture or detection moiety that is reactive against the target protein at an appropriate dilution. For example, the cells can be contacted with a capture moiety, such as an unconjugated primary antibody at an appropriate dilution (e.g., approximately 1:200 in approximately 20 mM sodium phosphate buffer, at about pH 7.4, containing about 150 mM sodium chloride, about 0.3% triton-X-100, and about 16% v/v filtered normal goat serum). The capture moiety can then be incubated for a desired period of time (e.g., approximately 10 minutes).

After incubation with the capture moiety, the membrane-bound cells can be washed any number of times (e.g., three times) with a buffered solution (e.g., PBS containing about 0.1 mM calcium chloride, about 1 mM magnesium chloride, about 0.3% triton-X-100, and about 0.1% bovine serum albumin). Next, the membrane-bound cells can be contacted with a labeled detection moiety that is reactive against the capture moiety, such as a fluorescently-conjugated secondary antibody that specifically binds to the primary antibody. The labeled detection moiety can be contacted with the membrane-bound cells at a desired dilution (e.g., about 1:200 in about 20 mM sodium phosphate buffer, at about Ph 7.4, containing about 150 mM sodium chloride, about 0.3% triton-X-100, and about 16% v/v filtered normal goat serum) and for a desired period of time.

The membrane-bound cells can then be washed any number of times (e.g., three times) with a buffered solution (e.g., PBS containing about 0.1 mM calcium chloride, about 1 mM magnesium chloride, about 0.3% triton-X-100, and about 0.1% bovine serum albumin). Next, the cells labeled with the detection moieties can be detected using a commercially available florescence microscope, such as the Leica TCS STED CW (Leica Microsystems Inc., Bannockburn, Ill.). Advantageously, the use of a pressure-assisted regimen (i.e., the SNAP i.d. protein detection system) for IHC analysis on cells cultured using a modified chamber slide system significantly decreases the time and volume of reagents needed for blocking, washing, and target protein detection.

Figure 4:
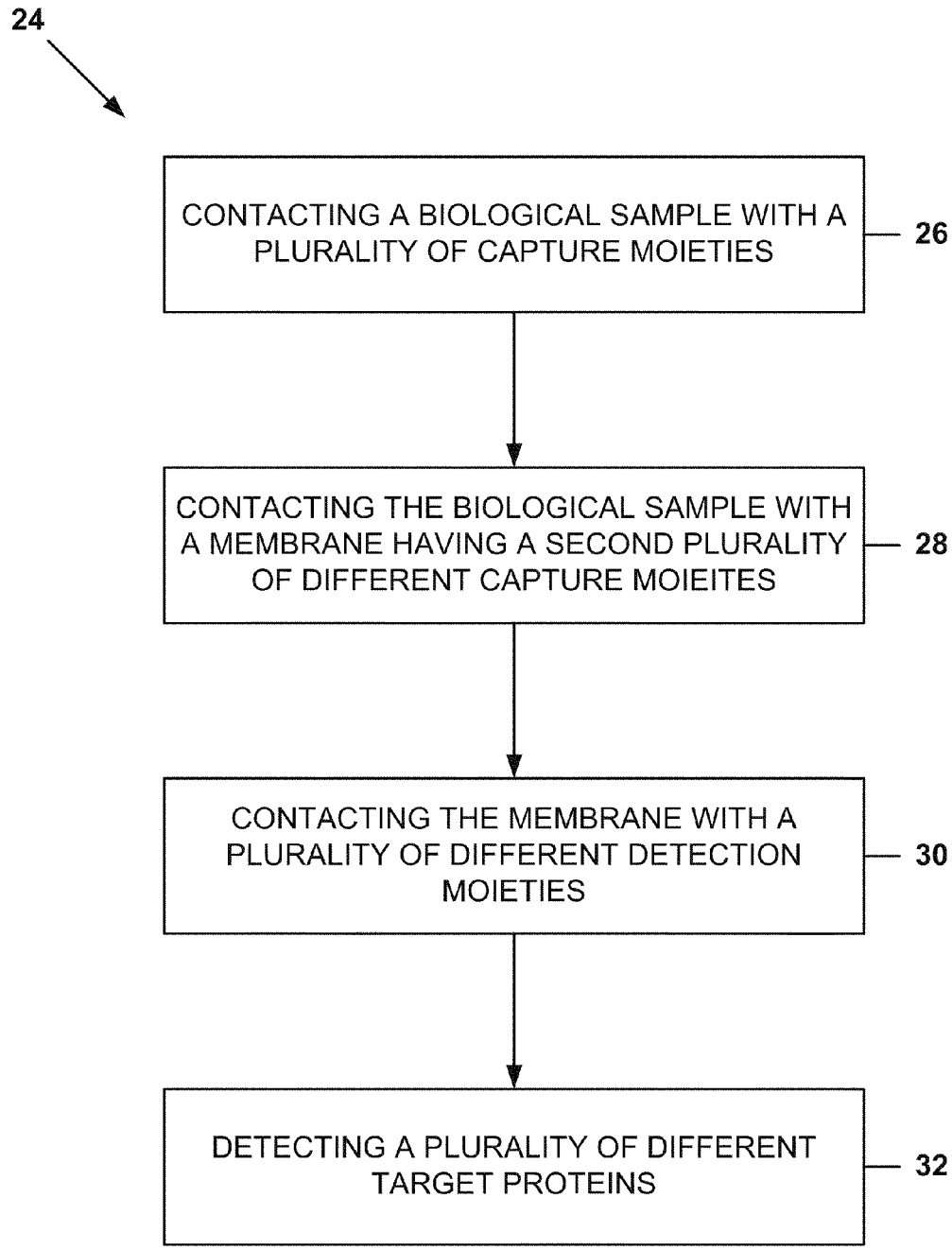
FIG. 4 is a process flow illustrating a method for detecting a plurality of different target proteins in a biological sample according to another aspect of the present invention.

Another aspect of the present invention is illustrated in FIG. 4. In FIG. 4, a method 24 is provided for detecting a plurality of different target proteins in a biological sample. At Step 26 of the method 24, the biological sample is contacted with a plurality of different capture moieties to form a cocktail. The biological sample can be obtained during a surgical procedure, such as a biopsy or fluid aspiration. For example, the biological sample can comprise a serum sample containing a plurality of different cytokines.

The plurality of different capture moieties is reactive against the plurality of different target proteins. For example, the plurality of different capture moieties can comprise a plurality of different biotinylated antibodies reactive against different cytokines in the serum sample, such as those commercially available in the PROTEOME PROFILER Mouse Cytokine Array Panel A Array Kit (R&D Systems, Inc., Minneapolis, Minn.). The cocktail is incubated at a desired temperature and for a sufficient amount of time to promote binding between the plurality of different capture moieties and the plurality of different target proteins. For example, the cocktail can be incubated at about room temperature for about 60 minutes to promote binding between a plurality of different biotinylated antibodies and the different cytokines present in the serum sample.

Either before, during, or after Step 26, a second plurality of different capture moieties is spotted or bound to at least one membrane having a first major surface oppositely disposed from a second major surface. The second plurality of different capture moieties is reactive against the plurality of different target proteins. For example, the second plurality of different capture moieties can comprise different antibodies reactive against different cytokines in the serum sample. The membrane can be comprised of any one or combination of porous materials suitable for protein immobilization, such as nitrocellulose, PVDF, and PES. For example, a plurality of different antibodies reactive against different cytokines can be spotted on the first major surface of a nitrocellulose membrane.

At Step 28, the membrane is transferred to a device capable of conducting at least one step of the method 24 as a pressure-assisted regiment (e.g., vacuum or positive gas pressure). For example, the membrane can be transferred to a SNAP i.d. holder. Prior to membrane transfer, however, the membrane is blocked using a suitable blocking reagent, such as the Array Buffer 6 commercially available from R&D Systems, Inc. (Minneapolis, Minn.). After transferring the membrane, the cocktail is contacted with the membrane for a desired period of time and then washed so that any target proteins (e.g., cytokines) that have been bound to their respective capture moiety (e.g., a biotinylated antibody) become bound to their immobilized cognate capture moiety (e.g., an antibody), which is present on the membrane. For example, the cocktail can be contacted with the membrane for approximately 10 minutes and then washed (e.g., approximately 3 times) with a wash buffer.

After washing the membrane, the membrane is contacted with a plurality of different detection moieties at Step 30. The plurality of different detection moieties is reactive against the plurality of different capture moieties. For example, the plurality of different detection moieties can comprise labeled antibodies (e.g., Streptavidin-HRP) reactive against the plurality of different capture moieties. The membrane can be contacted with the plurality of different detection moieties (e.g., Streptavidin-HRP-labeled antibodies) at a desired dilution (e.g., about 1:200 in Array Buffer 5, R&D Systems, Inc., Minneapolis, Minn.) and for a desired period of time (e.g., about 10 minutes) before washing with a 1× washing buffer.

At Step 32, the plurality of different target proteins is detected using an appropriate detection means. Where the detection moieties comprise Streptavidin-HRP-labeled antibodies, for instance, the plurality of different target proteins (e.g., cytokines) can be detected by contacting the membrane with at least one chemiluminescent reagent in the presence of a chemiluminescent film. For example, Amersham ECL PLUS reagents (GE Healthcare Bio-Sciences Corp., Piscataway, N.J.) can be contacted with the membrane and then detected via a chemiluminescent film. Alternatively, if the chemiluminescent reagent allows (e.g., a fluorescently-conjugated reagent), the plurality of different target proteins can be detected using a commercially available scanner, such as a LiCor ODYSSEY Infrared Imaging System (LI-COR Biotechnology, Lincoln, Nebr.) or a TYPHOON Laser Scanner (GE Healthcare Bio-Sciences Corp., Piscataway, N.J.).

Advantageously, the use of a pressure-assisted regiment (e.g., the SNAP i.d. protein detection system) for at least one step of the method 24 (e.g., Steps 28 and 30) significantly decreases the time and volume of reagents needed for blocking, washing, and capture/detection moiety binding. As compared to conventional protein detection assays (e.g., Western blots) where diffusion is the primary means of reagent transport, the supply and removal of reagents to and from the membrane under positive pressure or a vacuum enables completion of the blocking, washing, and capture/detection moiety binding steps in significantly reduced time without compromising blot quality.

The IHC method 10 of the present invention presents several advantages over current immunofluorescent (IF) techniques. Unlike IF, for example, one aspect of the present invention involves a peroxidase-based detection method (i.e., either the primary or secondary antibody can be conjugated to HRP), which can form a brown stain and be visualized with light microscopy. Conversely, with IF, the primary or secondary antibody is typically conjugated to a fluorophore, there is no chemical reaction catalyzed by HRP, and the end product is visualized by fluorescence microscopy, which requires highly specialized and expensive equipment. As compared to IF, the present invention is useful in the field of clinical pathology since the method 10 can not only be performed on formalin-fixed and fresh frozen specimens, but also may be readily visualized using light microscopy.

Current IHC analysis techniques require several sample handling and processing steps that are cumbersome and time consuming. Until the present invention, for example, it was difficult to handle tissue sections on a membrane, run several solutions/reagents over the samples via a vacuum manifold and still, at the end, maintain tissue integrity (i.e., no wrinkling, distortion, disintegration, etc. of the tissue section). The standard substrate for conventional IHC assays is glass due to its optical clarity. Unlike conventional IHC assays, however, the present invention provides membrane-based substrates that have reduced optical clarity yet, as illustrated in FIGS. 2A-3B and FIG. 5, surprisingly provide exceptional target molecule visualization.

The following examples are intended to illustrate aspects now known for practicing the present invention, but the invention is not to be considered limited to these examples.

Example 1

The method of the present invention was successfully performed using an OCT-embedded frozen section of a mouse liver transferred onto PVDF membranes. Eight micrometer frozen sections were transferred onto PVDF and allowed to bind with 30 minutes of drying at room temperature. The membranes were then rehydrated with PBS for 60 seconds and transferred to a SNAP i.d. blot holder (Millipore Corporation, Billerica, Mass.). The membrane-fixed tissue sections were then washed once with TBS-T for 20 seconds and then blocked using either 1% BSA dissolved in TBS-T or 1% normal goat serum dissolved in TBS-T. The membrane was then allowed to incubate with a primary for 10 minutes (Actin, rabbit polyclonal antibody, Santa Cruz Catalog # sc1616R, 1:200 dilution in 1% BSA/TBS-T) before washing 3 times with TBS-T for 60 seconds. Next, the membranes were incubated with the secondary fluorescently-conjugated antibody (goat anti-rabbit AlexaFluor 568, Molecular Probes Catalog # A-1101, 1:200 dilution in 1% BSA/TBS-T) for 10 minutes. The membranes were then washed again three times (60 seconds) and mounted on glass slides using VECTASHIELD mounting media with DAPI (Vector Laboratories, Burlingame, Calif.) (60 seconds). After this, a glass coverslip was placed over the sections and the coverslip sealed with acrylic nail polish. The sections were then taken to a microscope capable of fluorescent detection for visualization (FIGS. 2A-3B). As a control, some membrane-fixed sections were rehydrated with PBS and mounted directly using VECTASHIELD mounting media with DAPI with no antibody incubation. Also, some sections were only incubated with the secondary conjugated antibody. Fluorescent detection did not reveal interfering autofluorescence from the PVDF membrane following the SNAP i.d.-IHC procedure, which is surprising as PVDF membranes typically give high background fluorescence. In fact, the makers of the LiCor ODYSSEY Infrared Imaging System (LI-COR Biotechnology, Lincoln, Nebr.), which uses fluorescent dyes for Western blotting, suggests that users use nitrocellulose membranes instead of PVDF membranes for Western blotting experiments on the ODYSSEY system because of the known background autofluorescence problem.

Example 2

Figure 5:
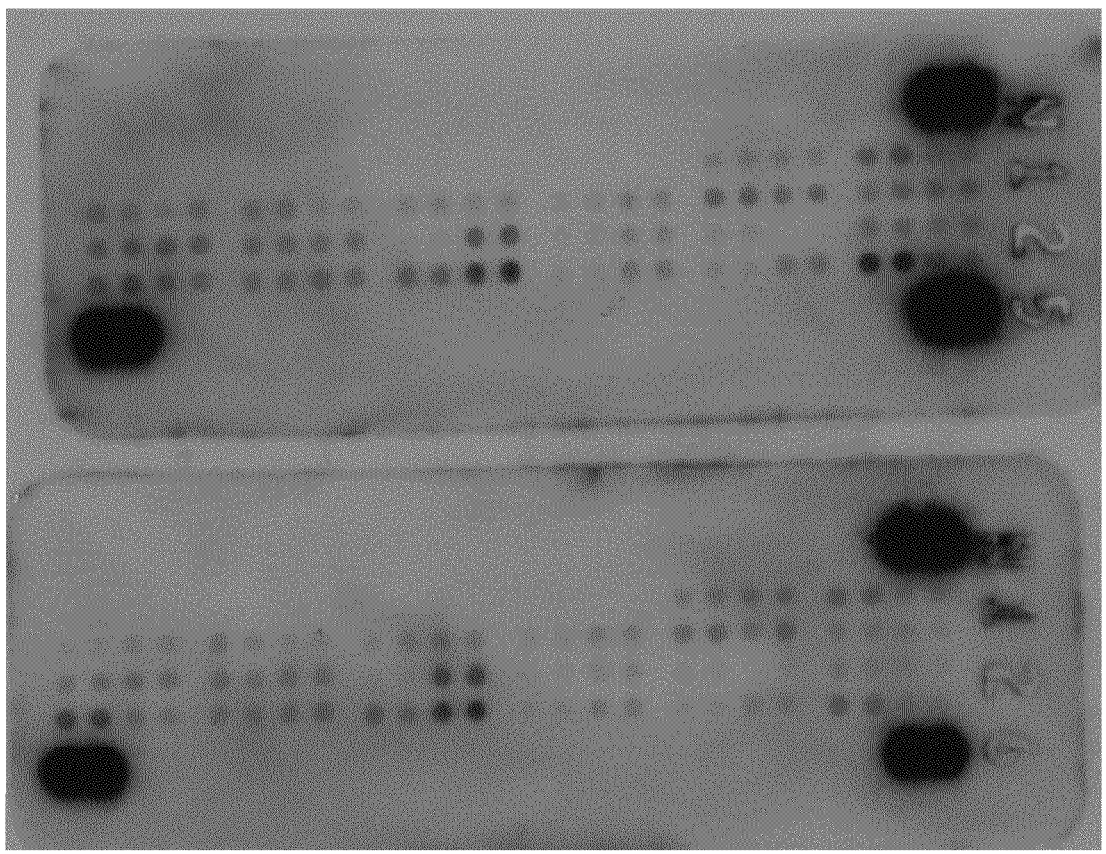
FIG. 5 is a chemiluminescent film showing detection of cytokine arrays using the R&D Systems Mouse Cytokine Array Panel A (R&D Systems, Inc., Minneapolis, Minn.) and the method illustrated in FIG. 4. Membrane arrays were prepared using mouse plasma, which was first incubated with a biotinylated antibody cocktail for 40 distinct cytokines for 60 minutes. After incubation, the plasma/biotinylated antibody cocktail mixture was applied to the membrane array for 10 minutes. All subsequent incubations, washes, and detection steps were performed under vacuum in the SNAP i.d. protein detection system (Millipore Corporation, Billerica, Mass.).

Capture antibodies provided from the PROTEOME PROFILER Mouse Cytokine Array Panel A Array Kit (R&D Systems, Inc., Minneapolis, Minn.) were spotted in duplicate on nitrocellulose membranes. Mouse serum samples were incubated with a biotinylated antibody mixture for 60 minutes at room temperature to form a cocktail. The array membranes were transferred to a SNAP i.d. blot holder and blocked with a blocking reagent (Array Buffer 6, R&D Systems, Inc., Minneapolis, Minn.) (20 seconds). Next, the cocktail was contacted with the membranes for 10 minutes in the SNAP i.d. blot holder and then washed three times with 1× wash buffer (60 seconds). The membranes were then allowed to incubate with a Streptavidin-HRP antibody for 10 minutes (1:2000 dilution in Array Buffer 5, R&D Systems, Inc., Minneapolis, Minn.) before washing three times with 1× wash buffer. Chemiluminescent detection reagents were added (AMERSHAM ECL PLUS, GE Healthcare Bio-Sciences Corp., Piscataway, N.J.) and detected with chemiluminescent film (FIG. 5).

From the above description of the invention, those skilled in the art will perceive improvements, changes and modifications. For example, it will be appreciated that more than one membrane-bound biological sample can be mounted to a substrate (e.g., a glass slide) at Step 20. Additionally, it will be appreciated that the present invention can be used for high-throughput applications. Such improvements, changes, and modifications are within the skill of the art and are intended to be covered by the appended claims.

Having described the invention, I claim:

1. A method for detecting a target molecule in a biological sample, said method comprising the steps of:
   (a) immobilizing the biological sample on a membrane;
   (b) contacting the membrane-bound biological sample with at least one detection moiety;
   (c) separately mating the membrane-bound biological sample with a substrate; and
   (d) detecting the target molecule with the at least one detection moiety;
   wherein at least one step of said method is performed under positive pressure or a vacuum.

2. The method of claim 1, wherein said step of immobilizing the biological sample on a membrane further comprises the steps of:

providing a membrane having a first major surface and an oppositely disposed second major surface;

contacting the biological sample with a portion of the first major surface so that the biological sample is bound to the first major surface; and applying a blocking solution to the membrane-bound biological sample.

3. The method of claim 1, wherein said step of immobilizing the biological sample on a membrane further comprises the steps of:

providing a membrane having a first major surface and an oppositely disposed second major surface;

immobilizing at least one capture moiety on the first major surface of the membrane; and applying a blocking solution to the membrane-bound biological sample.

4. The method of claim 1, wherein at least one of steps (a) and (b) is performed under positive pressure or a vacuum.

5. The method of claim 1, wherein said step of separately mating the membrane-bound biological sample with a substrate further comprises the step of mounting at least a portion of the membrane-bound biological sample on a glass microscope slide.

6. The method of claim 1, wherein the biological sample is a paraffin-embedded sample.

7. The method of claim 1, wherein the membrane is a polyvinylidene fluoride (PVDF) membrane.

8. An immunohistochemical method for detecting a target protein in a biological sample, said method comprising the steps of:

(a) immobilizing the biological sample on a membrane;

(b) contacting the membrane-bound biological sample with at least one detection moiety;

(c) separately mating the membrane-bound biological sample with a substrate; and (d) detecting the target protein with the at least one detection moiety;

wherein at least one step of said method is performed under positive pressure or a vacuum.

9. The method of claim 8, wherein said step of immobilizing the biological sample on a membrane further comprises the steps of:

providing a membrane having a first major surface and an oppositely disposed second major surface;

contacting the biological sample with a portion of the first major surface so that the biological sample is bound to the first major surface; and applying a blocking solution to the membrane-bound biological sample.

10. The method of claim 8, wherein said step of immobilizing the biological sample on a membrane further comprises the steps of:

providing a membrane having a first major surface and an oppositely disposed second major surface;

immobilizing at least one capture moiety reactive against the target protein on the first major surface of the membrane; and applying a blocking solution to the membrane-bound biological sample.

11. The method of claim 10 further comprising the steps of:

contacting the membrane-bound biological sample with at least one antibody reactive against the target protein;

mounting at least a portion of the membrane-bound biological sample on a glass microscope slide; and using a microscope to visualize the target protein.

12. The method of claim 8, wherein at least one of steps (a) and (b) is performed under positive pressure or a vacuum.

13. The method of claim 8, wherein the biological sample is a paraffin-embedded sample.

14. The method of claim 8, wherein the membrane is a polyvinylidene fluoride (PVDF) membrane.

* * * * *